(12) United States Patent
Steiner et al.

(10) Patent No.: US 8,846,577 B2
(45) Date of Patent: Sep. 30, 2014

(54) PHAGE DISPLAY USING COTRANSLATIONAL TRANSLOCATION OF FUSION POLYPEPTIDES

(75) Inventors: Daniel Steiner, Zürich (CH); Patrik Forrer, Dietikon (CH); Michael T. Stumpp, Zürich (CH); Andreas Plückthun, Zürich (CH)

(73) Assignee: University of Zurich, Zurich (CH)

( * ) Notice: Subject to any disclaimer, the term of this patent is extended or adjusted under 35 U.S.C. 154(b) by 1752 days.

(21) Appl. No.: 11/988,389

(22) PCT Filed: Jun. 30, 2006

(86) PCT No.: PCT/EP2006/063729
§ 371 (c)(1),
(2), (4) Date: Jan. 7, 2008

(87) PCT Pub. No.: WO2007/006665
PCT Pub. Date: Jan. 18, 2007

(65) Prior Publication Data
US 2011/0118146 A1      May 19, 2011

(30) Foreign Application Priority Data
Jul. 8, 2005   (EP) ..................... 05106236

(51) Int. Cl.
C40B 50/06    (2006.01)
C12N 15/10    (2006.01)

(52) U.S. Cl.
CPC ........ *C12N 15/1037* (2013.01); *C07K 2319/50* (2013.01); *C07K 2319/43* (2013.01); *C07K 2319/735* (2013.01); *C07K 2319/034* (2013.01)
USPC .......................................... 506/26

(58) Field of Classification Search
None
See application file for complete search history.

(56) References Cited

FOREIGN PATENT DOCUMENTS

WO    99/58655    11/1999

OTHER PUBLICATIONS

Barbas et al. (Sep. 15, 1991) Proceedings of the National Academy of Sciences USA vol. 88 pp. 7978 to 7982.*
Bothmann et al. (Apr. 1998) Nature Biotechnology vol. 16 pp. 376 to 380.*
Jestin (Feb. 2001) Research in Microbiology vol. 152 pp. 187 to 191.*
Kramer (Jun. 1, 2003) Nucleic Acids Research vol. 31 article e59 pp. 1 to 9.*
Huber (May 2005) Journal of Bacteriology vol. 187 pp. 2983 to 2991.*

(Continued)

*Primary Examiner* — Christian Boesen
(74) *Attorney, Agent, or Firm* — Wenderoth, Lind & Ponack, L.L.P.

(57) ABSTRACT

The present invention relates to a filamentous phage display method wherein the polypeptides of interest displayed on the phage particle are cotranslationally translocated across the cytoplasmic membrane of Gram-negative bacteria based on the signal recognition particle pathway. This method is particularly suitable for polypeptides, which are known to be difficult to display on phages, and for proteins of cDNA libraries and other combinatorial libraries, in particular when derived from very fast folding, stable protein scaffolds. The invention further relates to phage or phagemid vectors useful in the method comprising a gene construct coding for a fusion polypeptide comprising the polypeptide to be displayed on the phage particle and an N-terminal signal sequence promoting cotranslational translocation.

2 Claims, 6 Drawing Sheets

(56) References Cited

OTHER PUBLICATIONS

International Search Report issued Sep. 27, 2006 in the International (PCT) Application of which the present application is the U.S. National Stage.

A. Rosander et al., "Identification of Extracytoplasmic Proteins in *Bradyrhizobium japonicum* Using Phage Display", Molecular Plant-Microbe Interactions, vol. 16, No. 8, pp. 727-737, Aug. 2003.

T. Wall et al., "Phage Display Reveals 52 Novel extracellular and Transmembrane Proteins from *Lactobacillus reuteri* DMS 20016[T]", Microbiology, vol. 149, No. 12, pp. 3493-3505, Dec. 2003.

J. L. Jestin et al., "Improving the Display of Proteins on Filamentous Phage", Res. Microbiol., vol. 152, No. 2, pp. 187-191, Mar. 2001.

H. C. Lee et al., "The Targeting Pathway of *Escherichia coli* Presecretory and Integral membrane Proteins is Specified by the Hydrophobicity of the Targeting Signal", PNAS, vol. 98, No. 6, pp. 3471-3476, Mar. 13, 2001.

A. Rosander et al., "Phage Display as a Novel Screening Method to Identify Extracellular Proteins", Journal of Microbiological Methods, vol. 51, No. 1, pp. 43-55, Sep. 2002.

V. A. Petrenko et al., "A Library of Organic Landscapes on Filamentous Phage", Protein Engineering, vol. 9, No. 9, pp. 797-801, 1996.

D. Huber et al., "Use of Thioredoxin as a Reporter to Identify a Subset of *Escherichia coli* Signal Sequences that Promote Signal Recognition Particle-Dependent Translocation", Journal of Bacteriology, vol. 187, No. 9, pp. 2983-2991, May 2005.

C. F. Schierle et al., "The DsbA Signal Sequence Directs Efficient, Cotranslation Export of Passenger Proteins to the *Escherichia coli* Periplasma via the Signal recognition Particle Pathway", Journal of Bacteriology, vol. 185, No. 19, pp. 5706-5713, Oct. 2003.

\* cited by examiner

A)

B)

A)

B)

A)

B)

SEQUENCE LISTING

```
<160> NUMBER OF SEQ ID NOS: 16

<210> SEQ ID NO 1
<211> LENGTH: 19
<212> TYPE: PRT
<213> ORGANISM: Escherichia coli

<400> SEQUENCE: 1

Met Lys Lys Ile Trp Leu Ala Leu Ala Gly Leu Val Leu Ala Phe Ser
1               5                   10                  15

Ala Ser Ala

<210> SEQ ID NO 2
<211> LENGTH: 245
<212> TYPE: PRT
```

-continued

```
<213> ORGANISM: Artificial
<220> FEATURE:
<223> OTHER INFORMATION: Synthetic Construct; E1 - T245 of single-chain
      Fv binding gpD containing a disulfide bond

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Gly Gly Leu Met Asp Val Trp Gly Gln Gly Thr Leu Val
            100                 105                 110

Thr Val Ser Ser Ala Gly Gly Gly Ser Gly Gly Gly Ser Gly Gly
        115                 120                 125

Gly Gly Ser Gly Gly Gly Ser Asp Ile Gln Met Thr Gln Ser Pro
    130                 135                 140

Ser Ser Leu Ser Ala Ser Val Gly Asp Arg Val Thr Ile Thr Cys Arg
145                 150                 155                 160

Ala Ser Gln Gly Ile Ser Ser Tyr Leu Ala Trp Tyr Gln Gln Lys Pro
                165                 170                 175

Gly Lys Ala Pro Lys Leu Leu Ile Tyr Ala Ala Ser Ser Leu Gln Ser
            180                 185                 190

Gly Val Pro Ser Arg Phe Ser Gly Ser Gly Ser Gly Thr Asp Phe Thr
        195                 200                 205

Leu Thr Ile Ser Ser Leu Gln Pro Glu Asp Phe Ala Thr Tyr Tyr Cys
    210                 215                 220

Gln Gln Tyr Gly Ser Asp Pro Ile Thr Phe Gly Gln Gly Thr Lys Val
225                 230                 235                 240

Glu Ile Lys Arg Thr
                245

<210> SEQ ID NO 3
<211> LENGTH: 154
<212> TYPE: PRT
<213> ORGANISM: Artificial
<220> FEATURE:
<223> OTHER INFORMATION: Synthetic Construct; D13 - Q166 of DARPin 3a
      binding APH

<400> SEQUENCE: 3

Asp Leu Gly Lys Lys Leu Leu Glu Ala Ala Arg Ala Gly Gln Asp Asp
1               5                   10                  15

Glu Val Arg Ile Leu Met Ala Asn Gly Ala Asp Val Asn Ala Asn Asp
            20                  25                  30

Trp Phe Gly Ile Thr Pro Leu His Leu Val Val Asn Asn Gly His Leu
        35                  40                  45

Glu Ile Ile Glu Val Leu Leu Lys Tyr Ala Ala Asp Val Asn Ala Ser
    50                  55                  60

Asp Lys Ser Gly Trp Thr Pro Leu His Leu Ala Ala Tyr Arg Gly His
```

```
            65                  70                  75                  80
Leu Glu Ile Val Glu Val Leu Lys Tyr Gly Ala Asp Val Asn Ala
                    85                  90                  95

Met Asp Tyr Gln Gly Tyr Thr Pro Leu His Leu Ala Ala Glu Asp Gly
            100                 105                 110

His Leu Glu Ile Val Glu Val Leu Lys Tyr Gly Ala Asp Val Asn
            115                 120                 125

Ala Gln Asp Lys Phe Gly Lys Thr Ala Phe Asp Ile Ser Ile Asp Asn
    130                 135                 140

Gly Asn Glu Asp Leu Ala Glu Ile Leu Gln
145                 150
```

<210> SEQ ID NO 4
<211> LENGTH: 32
<212> TYPE: PRT
<213> ORGANISM: Artificial
<220> FEATURE:
<223> OTHER INFORMATION: Synthetic Construct; Peptide derived from
      transcription factor GCN4 (R249 to R281, E259-, S262P)

<400> SEQUENCE: 4

```
Arg Met Lys Gln Leu Glu Asp Lys Val Glu Leu Leu Pro Lys Asn Tyr
1               5                   10                  15

His Leu Glu Asn Glu Val Ala Arg Leu Lys Lys Leu Val Gly Glu Arg
            20                  25                  30
```

<210> SEQ ID NO 5
<211> LENGTH: 53
<212> TYPE: DNA
<213> ORGANISM: Artificial
<220> FEATURE:
<223> OTHER INFORMATION: Synthetic Construct; oDST4 oligonucleotide

<400> SEQUENCE: 5
agagcatgcg taggagaaaa taaaatgaaa aagatttggc tggcgctggc tgg          53

<210> SEQ ID NO 6
<211> LENGTH: 55
<212> TYPE: DNA
<213> ORGANISM: Artificial
<220> FEATURE:
<223> OTHER INFORMATION: Synthetic Construct; oDST5 oligonucleotide

<400> SEQUENCE: 6
tctttgtagt ccgccgatgc gctaaacgct aaaactaaac cagccagcgc cagcc       55

<210> SEQ ID NO 7
<211> LENGTH: 21
<212> TYPE: DNA
<213> ORGANISM: Artificial
<220> FEATURE:
<223> OTHER INFORMATION: Synthetic Construct; oDST6 oligonucleotide

<400> SEQUENCE: 7
gctctagagc atgcgtagga g                                             21

<210> SEQ ID NO 8
<211> LENGTH: 25
<212> TYPE: DNA
<213> ORGANISM: Artificial
<220> FEATURE:
<223> OTHER INFORMATION: Synthetic Construct; oDST8 oligonucleotide

<400> SEQUENCE: 8

```
gcggatccat ctttgtagtc cgccg                                         25
```

<210> SEQ ID NO 9
<211> LENGTH: 21
<212> TYPE: PRT
<213> ORGANISM: Escherichia coli

<400> SEQUENCE: 9

```
Met Lys Gln Ser Thr Ile Ala Leu Ala Leu Leu Pro Leu Leu Phe Thr
1               5                   10                  15

Pro Val Thr Lys Ala
            20
```

<210> SEQ ID NO 10
<211> LENGTH: 60
<212> TYPE: DNA
<213> ORGANISM: Artificial
<220> FEATURE:
<223> OTHER INFORMATION: Synthetic Construct; oDST4p oligonucleotide

<400> SEQUENCE: 10

```
agagcatgcg taggagaaaa taaaatgaaa caaagcacta ttgcactggc actcttaccg    60
```

<210> SEQ ID NO 11
<211> LENGTH: 59
<212> TYPE: DNA
<213> ORGANISM: Artificial
<220> FEATURE:
<223> OTHER INFORMATION: Synthetic Construct; oDST5p oligonucleotide

<400> SEQUENCE: 11

```
ccatctttgt agtcggcttt ggtaacaggg gtgaagagca acggtaagag tgccagtgc     59
```

<210> SEQ ID NO 12
<211> LENGTH: 23
<212> TYPE: DNA
<213> ORGANISM: Artificial
<220> FEATURE:
<223> OTHER INFORMATION: Synthetic Construct; oDST8p oligonucleotide

<400> SEQUENCE: 12

```
gcggatccat ctttgtagtc ggc                                           23
```

<210> SEQ ID NO 13
<211> LENGTH: 22
<212> TYPE: PRT
<213> ORGANISM: Erwinia carotovora

<400> SEQUENCE: 13

```
Met Lys Tyr Leu Leu Pro Thr Ala Ala Ala Gly Leu Leu Leu Leu Ala
1               5                   10                  15

Ala Gln Pro Ala Met Ala
            20
```

<210> SEQ ID NO 14
<211> LENGTH: 23
<212> TYPE: PRT
<213> ORGANISM: Escherichia coli

<400> SEQUENCE: 14

```
Met Met Thr Lys Ile Lys Leu Leu Met Leu Ile Ile Phe Tyr Leu Ile
1               5                   10                  15

Ile Ser Ala Ser Ala His Ala
```

```
<210> SEQ ID NO 15
<211> LENGTH: 21
<212> TYPE: PRT
<213> ORGANISM: Escherichia coli

<400> SEQUENCE: 15

Met Lys Gln Ala Leu Arg Val Ala Phe Gly Phe Leu Ile Leu Trp Ala
1               5                   10                  15

Ser Val Leu His Ala
            20

<210> SEQ ID NO 16
<211> LENGTH: 18
<212> TYPE: PRT
<213> ORGANISM: Escherichia coli

<400> SEQUENCE: 16

Met Arg Val Leu Leu Phe Leu Leu Leu Ser Leu Phe Met Leu Pro Ala
1               5                   10                  15

Phe Ser
```

PHAGE DISPLAY USING COTRANSLATIONAL TRANSLOCATION OF FUSION POLYPEPTIDES

This application is a U.S. national stage of International Application No. PCT/EP2006/063729 filed Jun. 30, 2006.

FIELD OF THE INVENTION

The present invention relates to a novel phage display method, phage or phagemid vectors used therein and the phage particles so obtained.

BACKGROUND OF THE INVENTION

Display of polypeptides on bacteriophage (phage display) is a selection technique that allows to extract polypeptides with desired properties from a large collection of variants (Russel, M., Lowman, H. B., and Clackson, T., Introduction to phage biology and phage display, in "Phage Display"; Clackson, T. and Lowman, H. B., eds., Oxford University Press, 2004, pp. 1-26). Phage display has been intensively investigated for the selection from combinatorial antibody or peptide libraries.

By far the most widely used bacteriophages used in phage display are filamentous phages. Filamentous phages constitute a large family of bacterial viruses that infect many Gram-negative bacteria. The best-known filamentous phages are those that infect *Escherichia coli*; these are f1/M13/fd and IKe. Phages f1, M13, and fd are those that have so far been used for filamentous phage display. Their genomes are more than 98% identical and their gene products are interchangeable.

A unique aspect of filamentous phage assembly, in contrast to the assembly of many other bacteriophages, is that it is a secretory process. Incorporation of coat polypeptides into the growing phage occurs in the cytoplasmic membrane, and nascent phages are extruded from the cell as they assemble (Russel et al., loc. cit.). The *E. coli* cell does not lyse in this process. The five viral coat proteins (pIII, pVI, pVII, pVIII and pIX) are inserted in the cytoplasmic membrane prior to their incorporation into phage particles (FIG. 1). For example, the major part of pIII is translocated across the membrane into the periplasm, while its C-terminal hydrophobic tail anchors the protein in the membrane.

One prerequisite for filamentous phage display is the translocation of the polypeptide of interest (POI) across the cytoplasmic membrane. This is normally achieved by genetically fusing the POI to a phage coat protein and translocation of the corresponding fusion polypeptide. Alternatively, the POI and phage coat protein are translocated independently.

In this situation the POI is stably linked to the phage particle in the periplasm by, for example, formation of a disulfide bond (Cys-Display) or formation of a leucine-zipper (pJuFo system) with a corresponding phage coat protein. In conventional filamentous phage display using fusions to pIII, the Sec pathway is used for translocation of the fusion polypeptide comprising the POI. In this pathway, the polypeptide is first synthesized at the ribosome and then posttranslationally translocated, in its unfolded state, by the Sec translocon (FIG. 2, (3)-(4)-(5)). That is, the translocation across the cytoplasmic membrane begins only after a substantial amount of the polypeptide chain has been synthesized. However, the contribution of the mechanism of translocation for the success of phage display has not been fully elucidated, and the possibility to use a cotranslational translocation pathway was not explored in the prior art.

Intracellular and extracellular proteins of a wide range of sizes and structures have been functionally displayed on filamentous phage (Russel et al., loc. cit.). Nevertheless, some polypeptides are recalcitrant to display due to individual properties, mostly because of unknown reasons. This makes the success of the display of a certain protein unpredictable. Thus, it has usually been recommended to first test the efficiency of display on filamentous phage for each protein to be used. In addition, when a combinatorial library is created for phage display, not all clones will display with similar efficiency; this is especially true for libraries generated from cDNAs. The display problems of polypeptides may be a result of their interference with the phage production, their periplasmic aggregation, their proteolysis, their toxicity to *E. coli* or their incompatibility with the used translocation pathway. Especially, the step preceding translocation is an important factor influencing the incorporation of the fusion polypeptides into the phage particles. If the polypeptides fold prematurely, they can be refractory to translocation or even exhibit cytoplasmic toxicity. Thus, it is important whether the protein is translocated posttranslationally (potentially allowing premature folding) or cotranslationally (not permitting cytoplasmic folding). Current filamentous phage display methods use posttranslational pathways for translocation of the fusion polypeptide across the cytoplasmic membrane (Russel et al., loc. cit.; Paschke, M. and Höhne, W., Gene 350, 79-88, 2005). Thus, polypeptides incompatible with these pathways will be refractory to display, making phage display selections very inefficient or even impossible. For example, the posttranslational Sec pathway, which is almost exclusively used in phage display, is inherently incapable of translocating proteins that cannot remain in an unfolded state in the cytoplasm, since the Sec translocon itself can only transport unfolded polypeptides (Huber, D., Boyd, D., Xia, Y., Olma, M. H., Gerstein, M., and Beckwith, J., J. Bacteriol. 187, 2983-2991, 2005; Paschke et al., loc. cit.).

Thus, the technical problem underlying the present invention is to identify novel translocation approaches for the efficient display of those polypeptides on filamentous phages that are displayed inefficiently by using posttranslational translocation. The solution to this technical problem is achieved by providing the embodiments characterized in the claims.

SUMMARY OF THE INVENTION

The present invention relates to a filamentous phage display method wherein the polypeptides of interest (POI) displayed on the phage particles are cotranslationally translocated across the cytoplasmic membrane of Gram-negative bacteria, in particular based on the signal recognition particle pathway.

Accordingly, the present invention allows phage display by cotranslational translocation of the fusion polypeptides comprising the POI. This method is particularly suitable for polypeptides, which are known to be difficult to display on phages, and for proteins of cDNA libraries and other combinatorial libraries, in particular when derived from very fast folding, stable protein scaffolds.

The invention further relates to phage or phagemid vectors comprising a gene construct coding for a fusion polypeptide comprising the POI to be displayed on the phage particle and an N-terminal signal sequence promoting cotranslational translocation based on the signal recognition particle pathway, and to phages obtained by the method of the invention.

N-termini (N), C-termini (C), polypeptide of interest (POI); N-terminal domains of pIII (N1, N2), C-terminal domain of pIII (CT).

A) The display of the polypeptide of interest (POI) on a filamentous phage particle always includes translocation of the POI across the cytoplasmic membrane (cm) into the periplasm (pp). Most often, the POI is translocated as a fusion polypeptide including the coat protein III (pIII) or a fragment thereof. pIII comprises two N-terminal domains (N1, N2) and the C-terminal domain (CT). In this specific example, the fusion polypeptide consists of the N-terminal POI and the C-terminal CT. The fusion polypeptide and pIII are anchored to the cytoplasmic membrane through a C-terminal hydrophobic stretch at the CT moiety after translocation and prior to their incorporation into the phage particle. Cytoplasm (cp), outer membrane (om), extracellular space (ex).

B) A simplified view of a filamentous phage particle displaying pIII and the fusion polypeptide of A). The N-terminal domains of pIII (N1, N2) and the POI are incorporated into the phage particle via the CT moiety.

Figure 2:
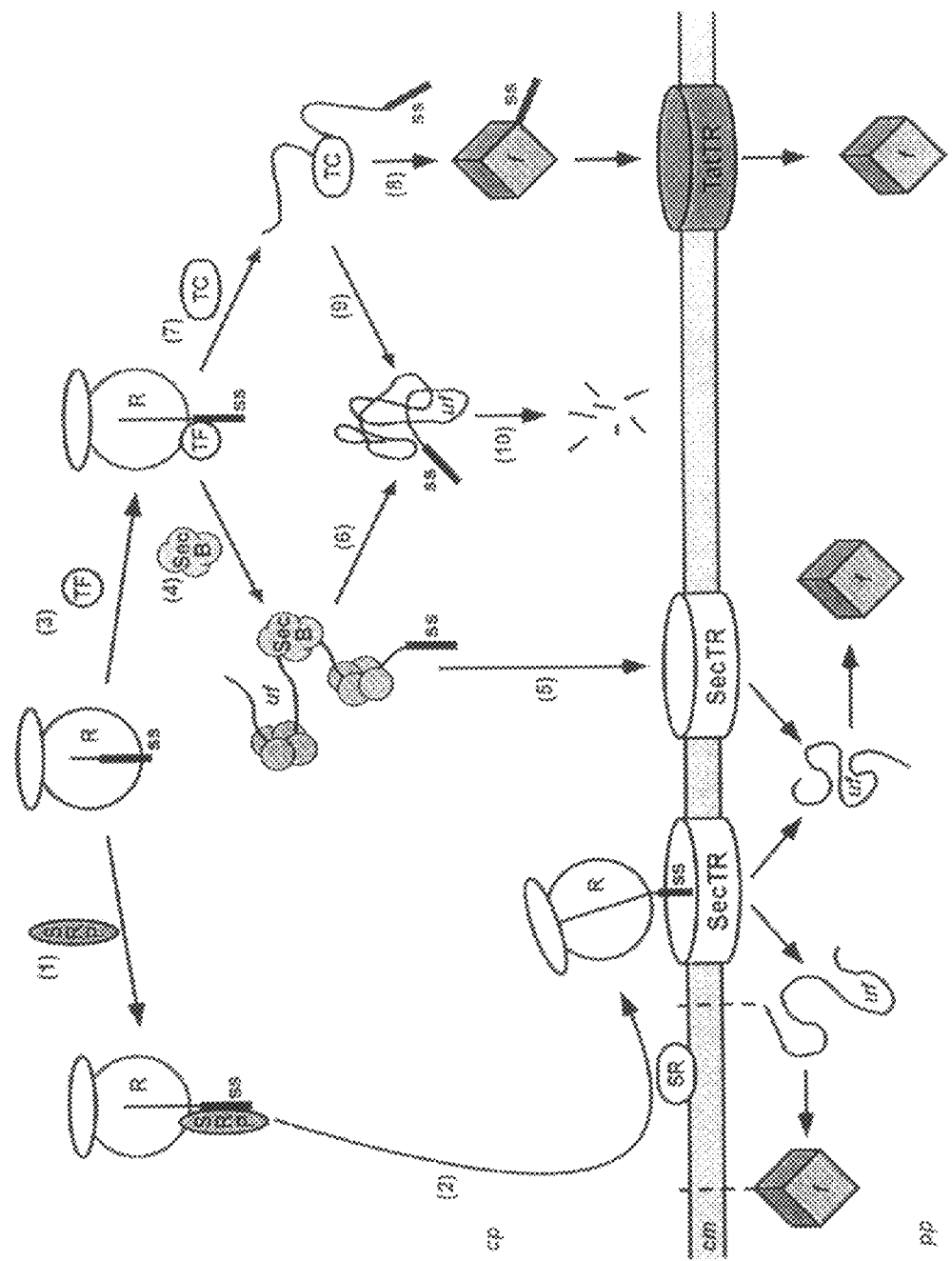

FIG. 2. Translocation of Polypeptides Across the Cytoplasmic Membrane of Gram-Negative Bacteria.

A simplified view of the three major pathways known for the translocation of polypeptides across the cytoplasmic membrane (cm) into the periplasm (pp) of Gram-negative bacteria. These pathways are the SRP pathway, the Sec pathway and the Tat pathway. Both the Sec and the SRP pathway rely on the Sec translocon (SecTR), whereas the Tat pathway relies on the Tat translocon (TatTR). Both the Sec and the Tat pathway translocate polypeptides posttranslationally whereas the SRP pathway translocates polypeptides cotranslationally. The Sec and SRP pathways converge at the Sec translocase that transports the proteins in an unfolded (uf) state through the membrane. In contrast, the Tat translocon only translocates folded (f) proteins. The amino acid composition of the signal sequence (ss) strongly favors the targeting of the preprotein to one of these pathways. After translocation, the signal sequence is cleaved off from the preprotein by a peptidase. The SRP pathway is mediated by the signal recognition particle (SRP), a ribonucleoprotein consisting of the 54-kDa protein homolog and a 4.5S RNA. In this pathway, it is the SRP that targets the preprotein to the Sec translocon. The SRP recognizes and binds corresponding signal sequences emerging from the ribosome (R), delivers the ribosome-nascent chain complex to the SRP-receptor (SR) and subsequently, the preprotein is cotranslationally translocated through the Sec translocon. Polypeptides that are incompatible with the Sec pathway because of their premature cytoplasmic folding can thus be efficiently translocated by the SRP pathway while being translated. (1) The SRP binds to particularly hydrophobic signal sequences of nascent proteins emerging from the ribosome. (2) The SRP directs the ribosome nascent chain complex via the SRP-receptor to the Sec translocon, were the cotranslational translocation takes place. Most preproteins have less hydrophobic signal sequences and undergo SecB dependent export. (3) Trigger factor (TF), a cytosolic chaperone that has a general affinity for nascent polypeptides, binds to the mature region of nascent preproteins and remains effectively bound until the translation is almost finished. (4) Following TF dissociation, cytosolic factors such as SecB help to maintain preproteins in an extended unfolded conformation. (5) Preproteins that retain an extended conformation are efficiently transported trough the Sec translocon. (6) However, if folding of the preprotein occurs in the cytoplasm, the protein is usually degraded (10) or may even plug up the Sec translocon.

Preproteins with signal sequences containing the twin-arginine motif are destined to the Tat translocon. (7) Association with a chaperone (TC), such as DnaK or another Tat-specific factor, probably shields the signal sequence until folding is completed (8). This same factor or an additional factor may also promote correct folding. Tat translocation proceeds only if the preprotein is correctly folded; otherwise, the preprotein is degraded by the proteolytic machinery (9, 10) of the cell.

Figure 3:
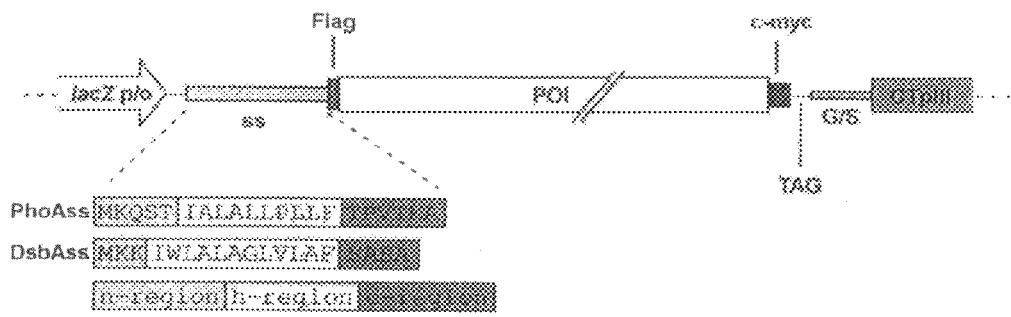
Figure 3:
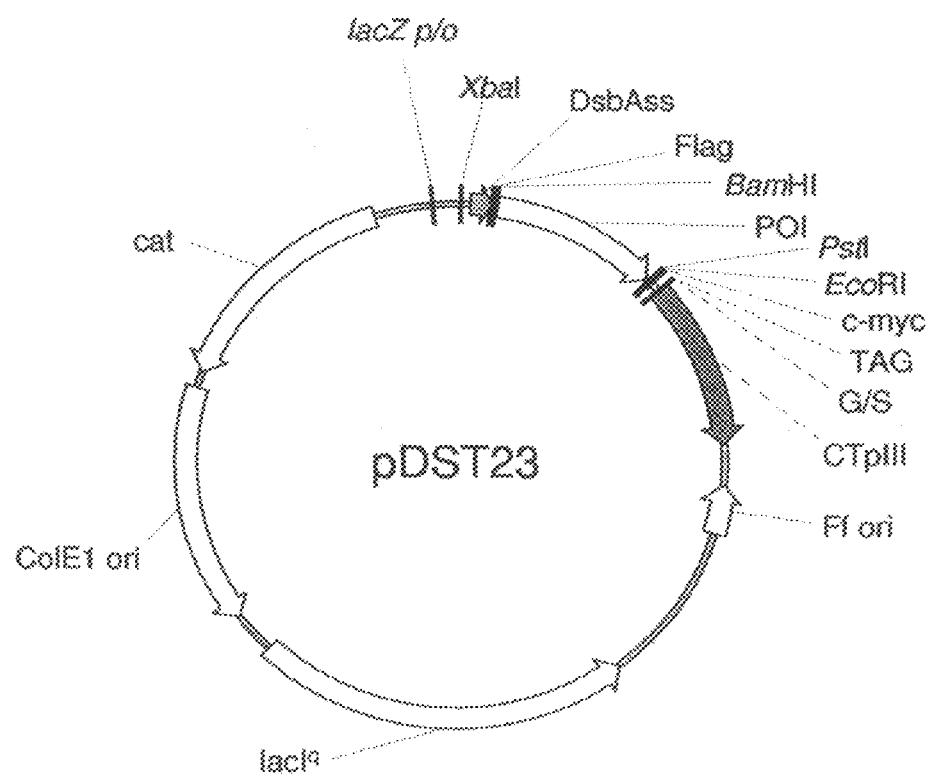

FIG. 3. Schematic Representation of the pDST Phagemid Vector Series.

A) Enlarged view of the expression cassette of the pDST phagemid vector series. The expression cassette comprises a promoter/operator element of the lacZgene of E. coli (lacZ p/o), a ribosome binding site (not depicted), the coding sequences for the signal sequence (ss) and a polypeptide of interest (POI) to be displayed, a suppressor stop codon (TAG), the coding sequences fora flexible glycine/serine linker (G/S) and for the C-terminal domain (amino acids 250-406) of protein III of filamentous phage (CTpIII) mediating incorporation of the fusion polypeptide into the phage particle, two stop codons (TGATAA, not depicted) and a transcription terminator element (not depicted). The coding sequence of the POI is flanked by DNA sequences encoding a Flag-tag (Flag) and a c-myc-tag (c-myc). The single letter amino acid sequences for the DsbA signal sequence (DsbAss) as a representative of signal sequences targeting the SRP pathway and for the PhoA signal sequence (PhoAss) as a representative of a signal sequences targeting the Sec pathway are shown. These signal sequences contain a positively charged N-terminal region (n-region), an apolar hydrophobic core (h-region) and a more polar C-terminal region (c-region).

B) Schematic representation of the phagemid pDST23. In addition to the elements shown in A) the filamentous phage replication origin (Ff ori), the lac repressor gene from E. coli (lacI), which produces lac repressor needed for the tight control of the lacZ p/o, the ColE1 origin of replication (ColE1 ori) for bacterial replication of the vector, the antibiotic resistance gene (cat) encoding a chloramphenicol-acetyl-transferase mediating chloramphenicol resistance and the restriction sites XbaI, BamHI, PstI, and EcoRI are depicted. The in pDST23 encoded POI is the designed ankyrin repeat protein (DARPin) 3a.

Figure 4:
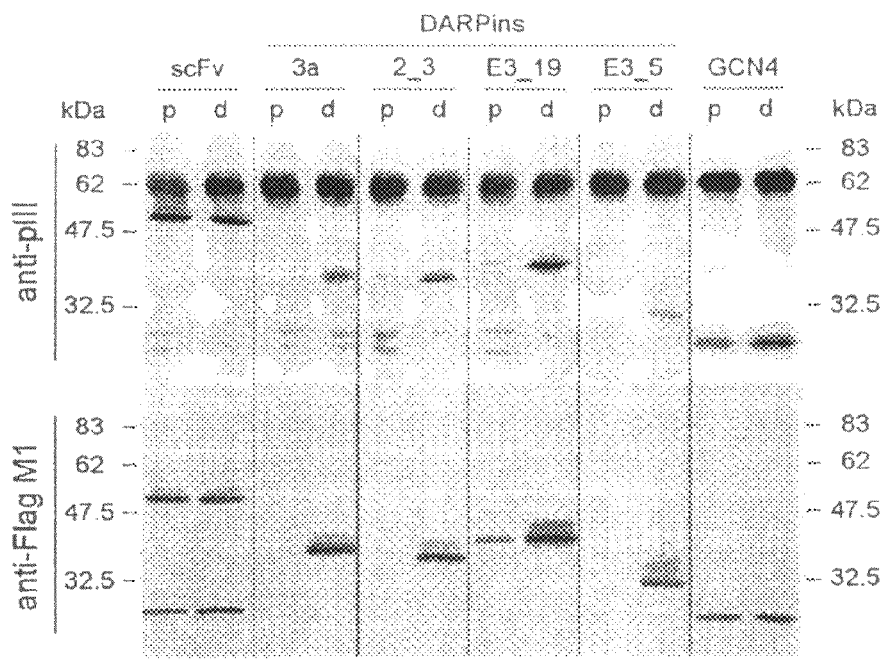
Figure 4:
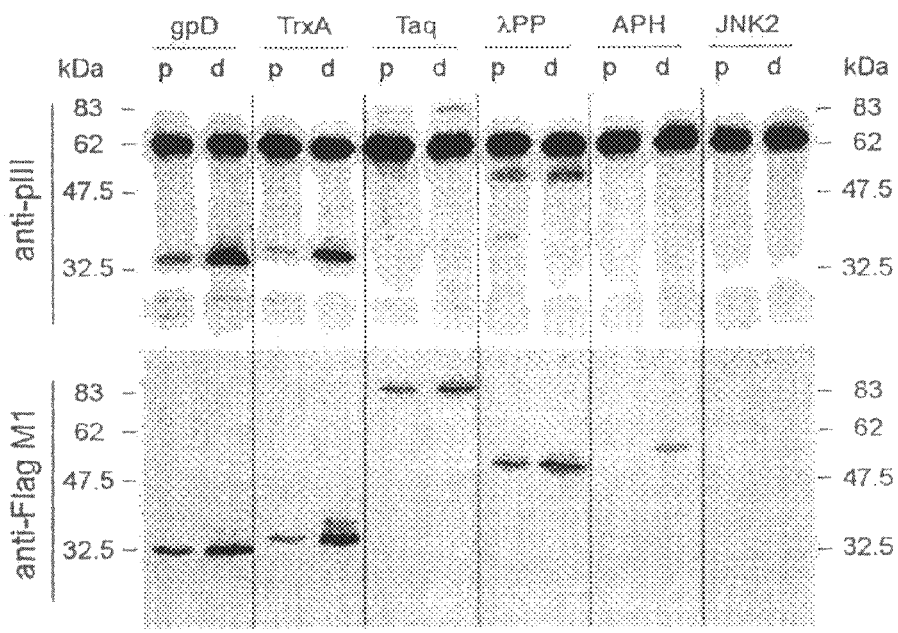

FIG. 4. Display Yield Comparison by Western Blot Analysis

A) and B) CsCl-purified phage particles produced by the use of the respective phagemids were separated by SDS-PAGE, blotted onto PVDF membranes and detected with antibodies specific for the C-terminal domain of protein III (anti-pIII) or the Flag-tag (anti-FlagM1). Aliquots applied per lane have been normalized and correspond to $5 \times 10^{11}$ phage particles. The display yields on phage particles for various polypeptides are analyzed. The abbreviated names of the polypeptides are indicated on top of the lanes and refer to the polypeptides listed in Table 1. In addition, Table 1 indicates the corresponding phagemids used to produce the phage particles, and an outline of the expression cassette is given in FIG. 3A. The display yields are compared for each polypeptide using either the PhoA signal sequences (lanes labeled "p") or the DsbA signal sequence (lanes labeled "d") to translocate the corresponding fusion polypeptide by the Sec pathway or the SRP pathway, respectively. Stronger bands indicate higher display yields. The molecular weights of marker proteins in kDa are indicated at both sides of the blot. The band at 62 kDa in the anti-pIII blot corresponds to the pIII wild-type protein.

Figure 5:
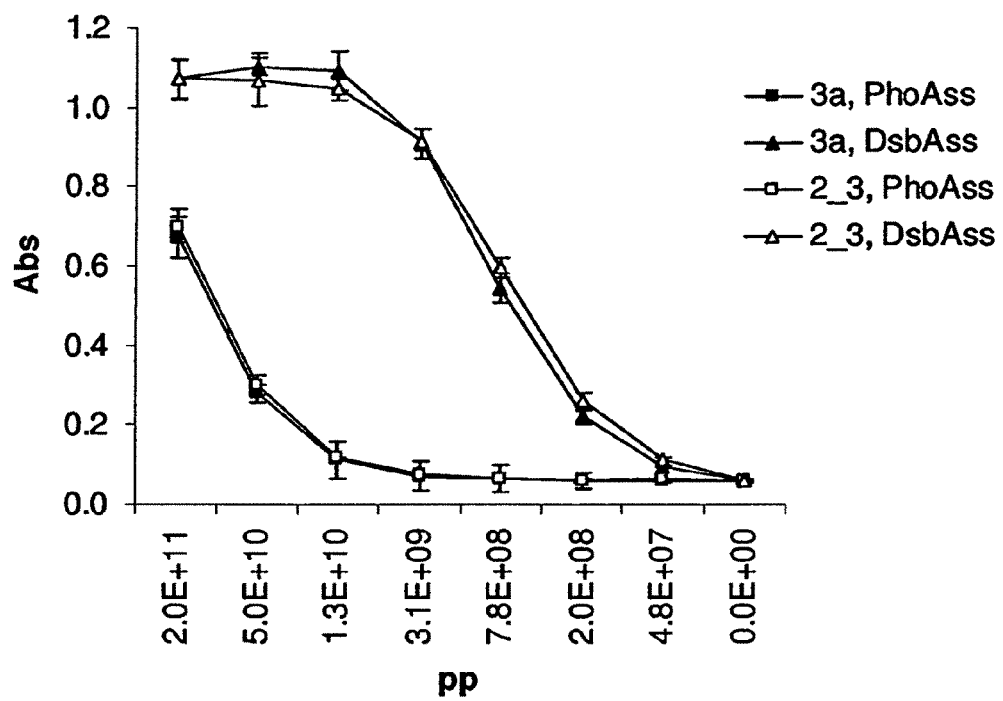

FIG. 5. Display Yield Comparison by ELISA Analysis

Phage particles displaying either the cJun N-terminal kinase 2 (JNK2)-binding. DARPin called 2_3 (open symbols) or the aminoglycoside kinase APH(3')-IIIa (APH)-binding DARPin called 3a (filled symbols) were incubated in neutravidin coated and BSA-blocked wells containing immobilized biotinylated JNK2 or APH proteins, respectively. After washing, the bound phage particles were detected with anti-M13 antibody coupled to horseradish peroxidase and visualized with soluble BM Blue POD substrate. The data plotted show the absorbance (Abs) on the y-coordinate measured at 360 nm after subtracting the background measured at 392 nm versus the number of phage particles (pp) applied per well on the x-axis. Phage particles produced using the DsbA signal sequence encoding phagemid variants (triangle symbols) showed half-maximum signal already at about $8 \times 10^8$ phages per well, whereas phage particles produced from PhoA signal sequence encoding variants (square symbols) showed half-maximum signal only at about $2 \times 10^{11}$ phage particles per well, indicating more than 100-fold lower display yields. Thus, the use of DsbA signal sequence-mediated SRP pathway for the translocation of the fusion polypeptides strongly increased the display yields in comparison to using the PhoA signal sequence-mediated Sec pathway.

Figure 6:
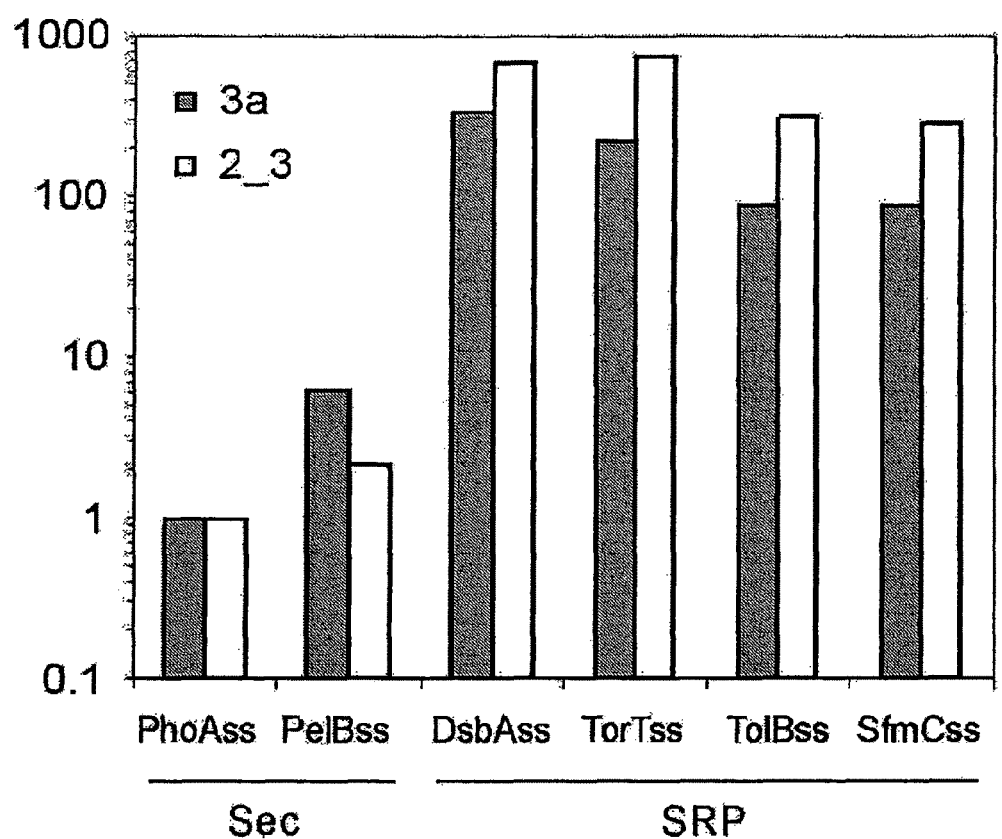

FIG. 6. Quantification of Display Yield by ELISA Analysis

Phage particles displaying DARPin 2_3 or 3a were analyzed as described for FIG. 5. The results are given in a column diagram (logarithmic scale) with PhoAss display yields set to 1. The display level (fold increase) for each signal sequence used corresponds to the number of phage particles giving a signal of $OD_{450}=0.5$ relative to the number of PhoAss-containing phage particles giving a signal of $OD_{450}=0.5$. PelBss: Signal sequence of *Erwinia carotovora* PelB (a putative Sec-dependent signal sequence). SRP-dependent signal sequences of the *E. coli* proteins TorT (TorTss), TolB (TolBss) and SfmC (SfmCss) were tested in addition to the DsbAss. An increased display yield of up to 700-fold was observed with the SRP-dependent TorTss compared to the Sec-dependent PhoAss. The SRP-dependent TolBss and SfmCss gave an increased display yield up to 300-fold. The putative Sec-dependent PelBss showed only a two- to sixfold increased display yield.

DETAILED DESCRIPTION OF THE INVENTION

In the context of the present invention, the term "filamentous phage display" refers to phage display based on filamentous phages. Filamentous phages constitute a large family of bacterial viruses that infect many Gram-negative bacteria. Preferred filamentous phages are those that infect *E. coli;* in particular f1/M13/fd and IKe. Methods to practice filamentous phage display are well known to the person skilled in the art (e.g. Russel et al., loc. cit.).

In the context of the present invention, the term "signal sequence" refers to an N-terminal stretch of amino acids of a polypeptide resulting in targeting of the polypeptide to a translocase. In *E. coli*, N-terminal signal sequences generally comprise 15 to 52 amino acids. Most signal sequences contain a positively charged N-terminal region (n-region), an apolar hydrophobic core (h-region) and a more polar C-terminal region (c-region). The c-region contains the cleavage site for signal peptidase. Signal peptidase is a membrane-bound protease that removes the signal sequence from the polypeptide during the translocation reaction. Such signal sequences comprising 18 to 30 amino acids are preferred. The determination of signal sequences is well known to the person skilled in the art. For example, they can be obtained from databases such as Swiss-Prot or GenBank or using annotated genome-wide data sets.

In the context of the present invention, the term "preprotein" refers to a polypeptide comprising an N-terminal signal sequence. The signal sequence is cleaved from the preprotein during the translocation reaction thus yielding the mature protein.

In the context of the present invention, the term "fusion polypeptide" refers to a polypeptide comprising an N-terminal signal sequence, the polypeptide of interest (POI) and an additional amino acid sequence allowing display on filamentous phage. Preferably, this additional sequence comprises a filamentous phage coat polypeptide or a fragment thereof. Alternatively, this sequence connects the POI to the phage particle in the periplasm by formation of a stable linkage, for example, by formation of a disulfide bond (Cys-Display) or by formation of a leucine-zipper (pJuFo system) with a corresponding phage coat protein. In this alternative strategy, the POI and the corresponding phage coat protein are translocated independently across the cytoplasmic membrane.

In the context of the present invention, the term "translocation" refers to the translocation of a polypeptide across a biological membrane mediated by a translocon (Holland, I. B. et al., Biochim. Biophys. Acta 1694, 5-16, 2004). The translocation occurs posttranslationally or cotranslationally. A translocase is hence an enzyme or enzyme complex that specifically transports a polypeptide through the translocon (Holland et al., loc. cit.).

In the context of the present invention, the term "Sec pathway" refers to a protein transport mechanism for posttranslational translocation of preproteins across the cytoplasmic membrane of Gram-negative bacteria through the Sec translocon (Holland et al., loc. cit.). The Sec pathway is mediated by molecular chaperones, most often SecB, that keep preproteins in an unfolded state before translocation. The Sec pathway is the major route of protein translocation in Gram-negative bacteria.

In the context of the present invention, the term "SRP pathway" refers to a protein transport mechanism for cotranslational translocation of preproteins across the cytoplasmic membrane of Gram-negative bacteria through the Sec translocon (Schierle, C. F., Berkmen, M., Huber, D., Kumamoto, C.; Boyd, D., and Beckwith, J., J. Bacteriol. 185, 5706-5713, 2003; Huber et al., loc. cit.). The SRP pathway is mediated by the signal recognition particle (SRP), a ribonucleoprotein consisting of the 54-kDa protein homolog (Fifty-four homolog; Ffh) and a 4.5S RNA. In the SRP pathway, the signal sequence interacts with SRP as soon as it appears from the ribosome. The complex consisting of SRP, nascent polypeptide and ribosome is then transferred via the SRP-receptor to the Sec translocon where the polypeptide is cotranslationally translocated through the Sec translocon.

The Sec and SRP pathways converge at the Sec translocase that transports the proteins in an unfolded state through the membrane. It is the amino acid composition of the signal sequence that will strongly favor the targeting of the preprotein to the SRP pathway over the Sec pathway for its translocation (Huber et al., loc. cit.).

In the context of the present invention, the term "DsbA" refers to the periplasmic *E. coli* thiol:disulfide interchange protein DsbA (Swiss-Prot accession number P24991). DsbA is a substrate of the SRP pathway (Huber et al., loc. cit.). DsbA is exported cotranslationally to avoid its folding in the cytoplasm, which would inhibit its export.

In the context of the present invention, the term "TrxA" refers to the *E. coli* protein thioredoxin 1 (Swiss-Prot accession number P00274). TrxA can be used as a reporter protein to distinguish signal sequences that target a preprotein to the SRP pathway or the Sec pathway (Schierle et al., loc. cit.; Huber et al., loc. cit.).

In the context of the present invention, the term "Tat pathway" refers to the twin-arginine protein translocation (Tat) pathway (Paschke et al., loc. cit.). The Tat pathway differs fundamentally from the Sec pathway and SRP pathway. In contrast to the Sec translocon, the Tat translocon exports only fully folded proteins. In contrast to the SRP pathway, the Tat translocon passes proteins posttranslationally through the membrane.

In one particular embodiment the signal sequence of the fusion polypeptide comprising the POI to be displayed on the phage particle is a signal sequence promoting cotranslational translocation.

Methods to test if a signal sequence of interest promotes cotranslational translocation across the cytoplasmic membrane of Gram-negative bacteria are well known to the person skilled in the art. For example, the signal sequence of interest is genetically fused to the mature MalE (Swiss-Prot accession number P02928, residues 27 to 396). This artificial preprotein is then expressed in *E. coli* and the yield of cotranslational proteolytic processing of its nascent chain is analyzed by two-dimensional gel electrophoresis as, described (Josefsson, L.-G. and Randall, L. L., Methods Enzymol. 97, 77-85, 1983; Schierle et al., loc.cit.). Removal of the N-terminal signal sequence of interest while the preprotein chains are still nascent indicates that translocation is initiated before the synthesis of the polypeptide is complete and thus that translocation is cotranslational. Preferred signal sequences are those that promote yields of cotranslational translocation of over 80%, more preferably over 90%, when fused to mature MalE. Most preferred signal sequences are those that do only promote cotranslational translocation and no posttranslational translocation when fused to mature MalE. Alternatively, signal sequences already known to promote cotranslational translocation, such as the signal sequence from DsbA, may be used.

In another particular embodiment, the signal sequence of the fusion polypeptide comprising the POI to be displayed on the phage particle is a signal sequence targeting the signal recognition pathway.

The signal recognition pathway of Gram-negative bacteria and methods to test if a signal sequence of interest targets a preprotein to the SRP pathway are well known to the person skilled in the art. For example, the translocation of TrxA fused to a signal sequence targeting the SRP pathway is strongly inhibited in *E. coli* bearing a mutation in the gene ffh (e.g. a ffh77 or ffh87 mutant strain), which encodes a component of the SRP (Schierle et al., loc. cit.; Huber et al., loc. cit.). Thus, those signal sequences that target the SRP pathway promote translocation of TrxA across the cytoplasmic membrane in wild-type *E. coli*, but very inefficiently in an ffh mutant strain. Signal sequences can thus be grouped into two distinct classes: Those that target the SRP pathway and those that do not target the SRP pathway. Signal sequences that target the Sec pathway can be redirected to the SRP pathway by increasing overall hydrophobicity of the signal sequence, in particular by increasing the hydrophobicity of its h-region. For example, modest alterations of the MalE signal sequence that simply increase its hydrophobicity by replacing polar or small (Gly or Ala) amino acids in the h-region by large hydrophobic residues reroute the protein from the Sec to the SRP pathway. Alternatively, signal sequences already known to target the SRP pathway, such as the signal sequence from DsbA, may be used. Other examples of signal sequences using the SRP pathway are those of a subset of autotransporters, such as that of the hemoglobin protease (Hbp, UniProtKB accession number O88093). Unusually, the Hbp signal sequence is relatively long (52 amino acids) and contains a N-terminal extension that precedes a classical signal sequence. In addition, the h-region of the Hbp signal sequence is not particularly hydrophobic. The signal sequence of SecM (Swiss-Prot accession number P62395) is another example of a long signal sequence that comprises an N-terminal extension and a moderately hydrophobic h-region that is known to target the SRP pathway.

In still another particular embodiment, the signal sequence of the fusion polypeptide comprising the POI to be displayed on the phage particle is a signal sequence promoting translocation of TrxA across the cytoplasmic membrane of Gram-negative bacteria.

Many commonly used signal sequences, e.g. those of PhoA (Swiss-Prot accession number P00634) and MalE (Swiss-Prot accession number P02928), do only inefficiently promote the translocation of TrxA across the cytoplasmic membrane (Schierle et al., loc. cit.). In contrast, the signal sequence from DsbA promotes efficient translocation of TrxA. Subcellular fractionation of host cells expressing TrxA fused to the signal sequence of interest allows to discriminate those signal sequences that are able to promote translocation of TrxA across the cytoplasmic membrane into the periplasm from those that are not (Huber et al., loc. cit.). The quantity of TrxA in the periplasmic fraction describes the efficiency of the signal sequence to promote translocation of TrxA. Alternatively, signal sequences already known to promote translocation of TrxA, such as the signal sequence from DsbA, may be used.

In a preferred embodiment, the signal sequence of the fusion polypeptide comprising the POI to be displayed on the phage particle is a signal sequence selected from the group consisting of TorT, SfmC, FocC, CcmH, YraI, TolB, NikA, FlgI and DsbA, and homologs thereof.

In a particularly preferred embodiment, the signal sequence of the fusion polypeptide comprising the POI to be displayed on the phage, particle is a signal sequence selected from the group consisting of TorT, SfmC, TolB and DsbA.

In the context of the present invention, the term "homolog" of a signal sequence means an amino acid sequence with 70%, preferably 80%, and in particular 90% or more amino acid identity with any of the signal sequences mentioned hereinbefore, while conserving the overall charge, hydrophobicity and cleavage properties of the n-region, h-region and c-region of the signal sequence, respectively. Examples of such homologs are amino acid sequences wherein one, two, three or four, in particular one or two, amino acids are replaced by other amino acids, wherein one, two, three or four amino acids are deleted, or one or two amino acids are added, or combinations of replacements, deletions and additions as mentioned hereinbefore. In replacements of amino acids, apolar amino acids are preferably replaced by other apolar amino acids, e.g. Ile by Leu, Val, Ala, Trp, Phe or Met or vice versa, polar amino acids by other polar amino acids, e.g. Thr by Ser, Asn or Gln or vice versa, negative charged amino acids by other negative charged amino acids, e.g. Asp by Glu or vice versa, or positive charged amino acids by other positive charged amino acids, e.g. Lys by Arg or His or vice versa For example, for the preferred signal sequence of DsbA with the amino sequence MKKIWLALAG LVLAFSASA (SEQ ID NO:1), the replacement of amino acid Lys2 by Arg, Ala9 by Leu, Ala14 by Val and Ser16 by Thr is possible.

The signal sequences of TorT, SfmC, FocC, CcmH, YraI, TolB, NikA, FlgI and DsbA are known to promote cotranslational translocation of TrxA by targeting the SRP pathway, and possess, in most cases, a higher overall hydrophobicity compared to signal sequences targeting the Sec pathway (Huber et al., loc. cit.). The proteins have the following. Swiss-Prot accession numbers: TorT P38683, SfmC P77249, FocC P62609, CcmH P33925, YraI P42914, TolB P0A855, NikA P33590, FlgI P0A6S3, and DsbA P24991.

Hydrophobicity calculations alone do not allow to discriminate SRP dependent and non-SRP dependent signal sequences in the high hydrophobicity range (Huber et al., loc. cit.). Thus, features other than hydrophobicity (e.g. the structure of the signal peptide) influence the preference for one translocation pathway.

In a particularly preferred embodiment, the signal sequence is the DsbA signal sequence or any amino acid sequence possessing 90% identity with the DsbA signal sequence.

The method is applicable to any of the filamentous phage display methods, for example with phages f1, M13, fd and Ike, in particular f1, M13 and fd.

In particular, the method of the invention comprises the steps of
(a) constructing a filamentous phage or phagemid vector containing an expression cassette for a fusion polypeptide that possesses an N-terminal signal sequence promoting cotranslational translocation of the fusion polypeptide across the cytoplasmic membrane of Gram-negative bacteria;
(b) constructing a combinatorial library of phage or phagemid vectors by cloning of a DNA library encoding the polypeptides of interests into the expression cassette of the vector of step (a);
(c) transforming suitable Gram-negative bacteria with the library of vectors of step (b); and
(d) performing phage display selection cycles to separate phage particles based on the properties of the displayed proteins of interest.

In step (a), the filamentous phage or phagemid vector is constructed using standard methods of gene technology. For example, the signal sequence encoding part of the expression cassette for the fusion polypeptide of an established phage or phagemid vector is replaced by the coding sequence of said signal sequence using standard DNA techniques. Alternatively, a novel phage or phagemid vector containing an expression cassette for the fusion polypeptide containing said signal sequence is constructed de novo using general knowledge on the composition of such vectors (e.g. Russel et al., loc. cit) and standard DNA synthesis and assembly methods. Phage or phagemid vectors useful for that purpose are, for example, pAK100, pComb3, pEXmide3, pHEN1, pJuFo or pSEX. An example of such a phagemid vector (pDST23) is described in FIG. 3 and in the accompanying Example, as an illustration of the invention without limiting the invention to this-particular embodiment.

Preferably, the signal sequence of the fusion polypeptide in step (a) promotes translocation of the fusion polypeptide through the SRP pathway.

More preferably, the signal sequence of the fusion polypeptide in step (a) promotes the cotranslational translocation of TrxA.

In step (b), standard methods for the preparation of combinatorial libraries of vectors are used. For example, combinatorial DNA libraries encoding the proteins of interest are generated by random or site-directed mutagenesis, by DNA shuffling, by preparation of cDNA through amplification of cellular mRNA or by consensus design and then ligated into the expression cassette of said vector by standard DNA techniques.

In step (c), standard methods for the transformation of Gram-negative bacteria are used. For example, the bacteria are transformed by the combinatorial library of vectors of step (b) by electroporation or chemical means. Such methods are well known to the person skilled in the art.

In step (d), standard phage display selection cycles are performed. Such phage display selection cycles are well known to the person skilled in the art (e.g. Russel et al., loc. cit.).

Preferably, the property of the displayed polypeptide of interest of step (d) is specific binding to a target molecule of interest. In this case, phage particles displaying a POI binding to the target molecule are separated from phage particles displaying irrelevant polypeptides by applying the amplified phage particles in each selection cycle to the target molecule functionally immobilized on a surface, washing unbound phage particles away, eluting the bound phage particles and using the eluted phage particles as input for the amplification of phage particles of the next selection cycle.

It is understood that, whenever in the context of this invention, "a signal sequence" or "the signal sequence" is mentioned, such an expression also means "one or more", e.g. one, two, three or four, signal sequences of different composition. Using more than one signal sequences may be advantageous for particular applications, and is also within the ambit of this invention.

The invention further relates to a phage or phagemid vector comprising a gene construct coding for a fusion polypeptide comprising the POI fused to an N-terminal signal sequence promoting cotranslational translocation of TrxA, in particular a signal sequence that is selected from the group consisting of signal sequences from TorT, SfmC, FocC, CcmH, YraI, TolB, NikA FlgI, and DsbA, and homologs thereof, preferably selected from TorT, SfmC, TolB and DsbA. Most preferred is a phage or phagemid vector comprising the signal sequence DsbA or a homolog thereof.

Preferably, the fusion polypeptide comprises the POI fused to the phage coat protein pIII or pVIII, or to a fragment of the coat protein pIII. Such a fragment is, for example, a fragment comprising amino acids 250 to 406 of pIII.

The signal sequence of the periplasmic enzyme DsbA directs fused reporter proteins to the SRP pathway and thus enhances their cotranslational export. This indicates that the relatively hydrophobic DsbA signal peptide interacts with SRP and promotes cotranslational translocation of DsbA. Thus, the signal sequence of DsbA can be used as a generic signal sequence for other proteins, as will be shown below in the Example.

Likewise, homologs of the signal sequence of DsbA, and signal sequences of TorT, SfmC, FocC, CcmH, YraI, TolB, NikA, and FlgI and homologs thereof may be used.

The method of the invention is particularly suitable for the application with libraries of compounds, for example DNA libraries, in particular cDNA libraries. In contrast to methods used hitherto in phage display, the method of the invention allows reliable presentation of polypeptides obtained by expression of such libraries.

A particular embodiment of the invention is the described filamentous phage display method wherein POIs encoded by a DNA library are displayed on the phage particles. Preferably, cotranslational translocation for the POIs encoded by a DNA library is accomplished based on the signal recognition particle pathway, such as a signal sequence promoting cotranslational translocation of TrxA. Most preferred is the method as described herein for the phage display of repeat proteins.

As with any selection technology, the success of phage display selections strongly depends on the diversity of displayed library members. A large combinatorial DNA library does not by itself guarantee that a large diversity of library members can be displayed. In phage display, the polypeptides to be displayed have to be translocated across the cytoplasmic membrane before their incorporation into phage particles. Current filamentous phage display methods all use a posttranslational pathway for translocation of the fusion polypeptide across the cytoplasmic membrane (Russel et al., loc. cit.; Paschke et al., loc. cit.). Thus, library members incompatible with these pathways will be refractory to display thus clearly reducing the displayed library diversity.

DNA libraries considered are all possible combinatorial DNA libraries including those produced by random or site-directed mutagenesis, by DNA shuffling, or by consensus design. Such methods will generate library members with novel properties, such as binding properties; some of them will be incompatible with the translocation using the Sec pathway. Such libraries include DNA libraries that encode peptide libraries, antibody libraries or libraries based on alternative scaffolds (Russel et al., loc. cit.; Nygren, P. A. and Skerra, A., J. Immunol. Methods, 290, 3-28, 2004).

Further DNA libraries considered are cDNA libraries, especially those of eukaryotic origin. cDNA libraries encode a great variety of naturally occurring cellular proteins including cytoplasmic proteins, membrane proteins and extracellular proteins. Some of these naturally occurring library members will be incompatible with translocation using the Sec pathway.

Further DNA libraries considered are those encoding single-chain Fv (scFv) antibody libraries that are used to select intracellularly active scFv fragments (intrabodies). A prerequisite for intrabodies is that they fold well and are stable in the cytoplasm of E. coli. Thus, cytoplasmic-stable and well-folded intrabodies are inefficiently translocated by the posttranslational mechanism of the Sec pathway.

Further DNA libraries considered are those encoding alternative scaffold libraries based on repeat proteins, including ankyrin repeat proteins, leucine-rich repeat proteins, tetratricopeptide repeat protein, pentatricopeptide repeat proteins or armadillo/HEAT repeat proteins.

A preferred DNA library is a library encoding designed ankyrin repeat proteins (DARPins) (Binz, H. K., Amstutz, P., Kohl, A., Stumpp, M. T., Briand, C., Forrer, P., Grütter, M. G., and Plückthun, A., Nat. Biotechnol., 22, 575-582, 2004). Examples of DARPins displayed on phage particles are shown in the Example.

The invention further relates to the phages produced by the method of the invention.

The invention further relates to the periplasmic expression of very fast folding and cytoplasmically stable proteins, in particular to the periplasmic expression of DARPins. The DsbAss and DARPins encoding phagemids of the Examples can directly be used for the efficient periplasmic expression of the DARPins in a non-suppressing E. coli. Alternatively, standard periplasmic expression vectors can be adapted by replacing the DNA encoding the signal sequence used for periplasmic expression by DNA encoding a signal sequence of the current invention, in particular by the DNA encoding the DsbAss. For example, the efficient periplasmic expression of DARPins is instrumental to the expression of DARPins fused to effector proteins, in particular toxins or cytokines, which are very difficult to express in the cytoplasm.

Figure 1:
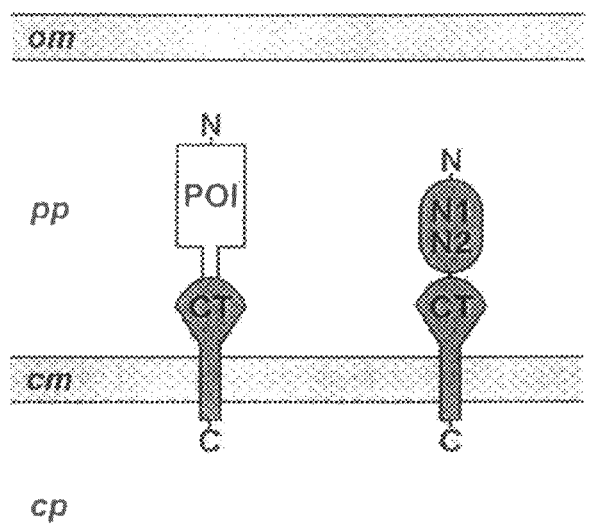
FIG. 1. Membrane Insertion and Display of the Polypeptide of Interest
Figure 1:
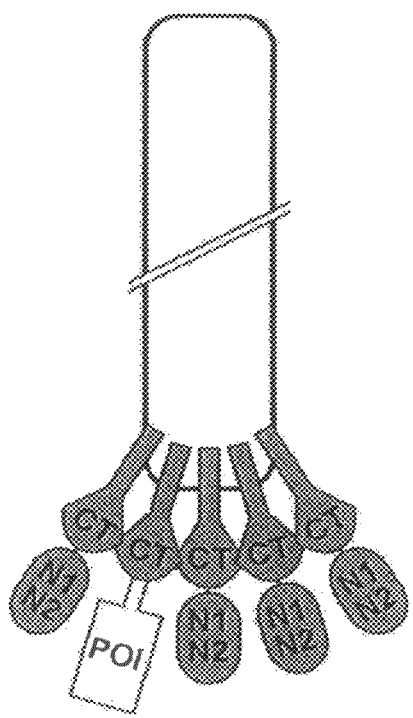

The new phage display method exemplified herein below allows to efficiently incorporate a very broad range of POIs to be displayed into phage particles and thus enables efficient phage display. The key difference of this new method compared to traditional phage display methods is the use of signal sequences directing the fusion polypeptide comprising the POI to be displayed to the cotranslational SRP pathway (FIG. 2, (1)-(2)). In this way, the POI to be displayed is efficiently translocated across the cytoplasmic membrane into the periplasm, thus enabling efficient incorporation of the POI into the phage particles. Preferred fusion proteins also comprise one of the filamentous phage coat proteins or truncated versions of the coat proteins. In this case, the POI is anchored to the cytoplasmic membrane by the hydrophobic extension of the phage coat protein after translocation (FIG. 1) and before incorporation into the phage particle.

One particular example of a signal sequence targeting the SRP pathway is the signal sequence of the E. coli protein DsbA (DsbAss). All other elements of the exemplified pDST phagemids are derived from classical phagemids such as the pAK100 series, which carry the signal sequences of PelB (PelBss) or the PhoA (PhoAss) directing the polypeptides of interest to be displayed via the posttranslational Sec pathway (FIG. 2, (3)-(4)-(5)).

In one series of experiments, the display yields were compared between phage particles produced from pDST phagemids encoding PhoAss and pDST phagemids encoding DsbAss. Phage particles were produced with standard protocols as described below and purified by CsCl gradient centrifugation. Western Blotting showed that for the display of a single-chain Fv antibody the pDST phagemid produced phage particles that have about the same display yields of the POI independent of the signal sequence used (FIG. 4A, scFv). In stark contrast however, all four tested DARPins could, only be efficiently displayed when using the DsbAss containing pDST phagemids, and almost no protein displayed could be detected when using the PhoAss containing pDST phagemids (FIG. 4A, DARPins). Similarly, the DsbAss containing pDST phagemids resulted in considerably higher display yields in case of the polypeptides GCN4 (FIG. 4A), lambda head protein D, TrxA and APH (FIG. 4B). Only slightly higher display yields were observed for proteins Taq polymerase, phage Lambda protein phosphatase (λPP): and no displayed protein could be detected in case of c-jun N-terminal kinase 2 (JNK2, FIG. 4B). This demonstrates that the display yields on phage particles produced by using DsbAss containing pDST phagemids are at least comparable to those produced by classical phagemids using PhoAss, but show strongly increased display yields when displaying DARPins and other rapid folded and thermodynamically stable proteins.

To quantify this difference, phage particles were used in phage ELISA experiments. Phage particles displaying DARPins specifically binding the proteins APH and JNK2 were compared after production from either DsbAss containing pDST phagemids or PhoAss containing pDST phagemids. Based on the detection of bound phage particles as quantified with an anti-M13 antibody, an increased display yield of more than 100-fold was observed (FIG. 5).

To demonstrate that the higher display yields obtained by using DsbAss also benefit selection experiments, two test mixtures containing three different types of phage particles produced from phagemids encoding either DsbAss or PhoAss were mixed in various dilutions. For both test mixtures phage particles displaying DARPins specifically binding the proteins APH and JNK2 were spiked at a $1:10^7$ dilution into phage particles displaying unselected DARPins E3_5 and E3_19. These two test mixtures were used as input libraries for standard phage display selections on the target proteins APH and JNK2 (Table 2). Whereas the APH and JNK2 specific phage particles could be enriched from the test mixtures produced from DsbAss-encoding phagemids around 1000-fold per selection cycle (already more than 10% of the tested clones were specific for their target after only two cycles of selection), no enrichment from the test library produced from PhoAss containing phagemids could be observed even after five selection cycles (no specific clones observed).

In another series of experiments, the display yields were compared by phage ELISA between phage particles produced from pDST phagemids encoding PhoAss, PelBss, DsbAss, TorTss, TolBss or SfmCss. Phage particles displaying DARPins specifically binding the proteins APH and JNK2 were compared after production from individual pDST phagemids. Based on the detection of bound phage particles as quantified with an anti-M13 antibody, an increased display yield of up to 700-fold was observed with the SRP-dependent signal sequences (DsbAss, TorTss, TolBss or SfmCss) compared to the Sec-dependent signal sequence PhoAss. (FIG. 6).

TABLE 2

Enrichment of DARPins 3a and 2_3 presenting phage[a]

| Antigen | Signal sequence of phagemid | Cycle of panning (Positive colonies/amount of colonies tested)[b] | | | | |
|---|---|---|---|---|---|---|
| | | 1st | 2nd | 3rd | 4th | 5th |
| APH | PhoAss | 0/11 | 0/15 | 0/14 | n.d. | 0/9 |
| | DsbAss | 0/14 | 4/16 | 14/14 | n.d. | n.d. |
| JNK2 | PhoAss | 0/14 | 0/16 | 0/14 | n.d. | 0/11 |
| | DsbAss | 0/14 | 2/16 | 14/14 | n.d. | n.d. |

[a]Input mixtures produced from phagemids encoding either PhoAss or DsbAss were produced as described in the Example. To a 1:1 mixture of phage particles displaying the unselected DARPins E3_5 and E3_19, phage particles displaying the target specific DARPins 3a or 2_3 were added in a 1:10$^7$ dilution.
[b]Colonies were screened by DNA sequencing

TABLE 1

Description of proteins displayed on the surface of filamentous bacteriophage

| Protein[a] | Abbr. | Phagemid PhoAss | Phagemid DsbAss | Description[b] | Ref. |
|---|---|---|---|---|---|
| scFv_gpD | scFv | pDST24 | pDST31 | E1 - T245 of single-chain Fv binding gpD containing a disulfide bond | c |
| DARPin 3a | 3a | pDST22 | pDST23 | D13 - Q166 of DARPin 3a binding APH | d |
| DARPin JNK2_2_3 | 2_3 | pDST34 | pDST37 | D13 - Q133 of DARPin JNK2_2_3 binding JNK2 | e |
| DARPin E3_5 | E3_5 | pDST30 | pDST32 | D13 - Q166 of unselected DARPin E3_5 | f |
| DARPin E3_19 | E3_19 | pDST65 | pDST66 | D13 - Q166 of unselected DARPin E3_19 | g |
| GCN4 | GCN4 | pDST39 | pDST40 | R249 - R281 of a peptide derived from transcription factor GCN4 (E259-, S262P) | h |
| pD□N2 | gpD | pDST41 | pDST42 | T21 - V110 of the capsid stabilizing protein of bacteriophage λ | i |
| JNK2□2 | JNK2 | pDST45 | pDST46 | S2 - R424 of mitogen-activated protein kinase JNK2 | j |
| TrxA | TrxA | pDST47 | pDST48 | S1 - A108 of thioredoxin (TrxA gene of *E. coli*) | k |
| Stoffel fragment Taq polymerase | Taq | pDST51 | pDST52 | S290 - E832 of Taq DNA polymerase | l |
| λ-phosphatase | λPP | pDST53 | pDST54 | M1 - A221 of bacteriophage λ Ser Thr protein phosphatase | m |
| APH | APH | pDST55 | pDST56 | A2 - F264 of aminoglycoside phosphotransferase (C19S, C156S, S194C) | n |

[a]scFv, single chain Fv antibody fragment; DARPin, designed ankyrin repeat protein; PhoAss, PhoA signal sequence; DsbAss, DsbA signal sequence
[b]The first and last amino acids used are indicated in single letter amino acid code, point mutations are mentioned
c (SEQ ID NO: 2)
d (SEQ ID NO: 3)
e Binz, H. K. et al. loc. cit.
f GenBank accession number AAO25689
g GenBank accession number AAO25690
h (SEQ ID NO: 4)
i Swiss-Prot accession number P03712
j Swiss-Prot accession number P45984
k Swiss-Prot accession number P00274
l Swiss-Prot accession number P19821
m Swiss-Prot accession number P03772
n Swiss-Prot accession number P0A3Y5

TABLE 3

Signal sequences

| Abbrev. | Source | SEQ ID NO | Swiss Prot Accession no. |
|---|---|---|---|
| DsbAss | E. coli thio-disulfide interchange protein DsbA | 1 | P0AEG4 |
| PhoAss | E. coli alkaline phosphatase PhoA | 9 | P00634 |
| PelBss | Erwinia carotovora pectate lyase PelB | 13 | P11431 |
| SfmCss | E. coli chaperone protein SfmC | 14 | P77249 |
| TolBss | E. coli protein TolB | 15 | P0A855 |
| TorTss | E. coli perimplasmic protein TorT | 16 | P38683 |

EXAMPLE

Materials

Chemicals were purchased from Fluka (Switzerland). Oligonucleotides were from Microsynth (Switzerland). Vent DNA polymerase, restriction enzymes and buffers were from New England Biolabs (USA) or Fermentas (Lithuania). Helper phage VCS M13 was from Stratagene (USA). All cloning and phage amplification was performed in E. coli XL1-Blue from Stratagene (USA).

Molecular Biology

Unless stated otherwise, all molecular biology methods were performed according to described protocols (Ausubel, F. M., Brent, R., Kingston, R. E., Moore, D. D., Sedman, J. G., Smith, J. A. and Stuhl, K. eds., Current Protocols in Molecular Biology, New York: John Wiley and Sons, 1999). Brief protocols are given below.

Phage Display Related Methods

Unless stated otherwise, all phage display related methods were performed according to described protocols (Clackson, T. and Lowman, H. B. eds., Phage Display A Practical Approach, New York: Oxford University Press, 2004; Barbas III, C. F., Burton, D. R., Scott, J. K. eds., Phage Display: A Laboratory Manual, Cold Spring Harbor Laboratory Press, 2001). Brief protocols are given below.

Cloning

A derivative of phagemid pAK100 (Krebber, A., Bomhauser, S., Burmester, J., Honegger, A., Willuda, J., Bosshard, H. R., and Plückthun, A., J. Immunol. Methods 201, 35-55, 1997) encoding the DARPin 3a was the starting point for the cloning of the first phagemid of this study, called pDST23.

To replace the signal sequence of this pAK100 derivative, the oligonucleotides oDST4 (SEQ ID NO:5), oDST5 (SEQ ID NO:6), oDST6 (SEQ ID NO:7), and oDST8 (SEQ ID NO:8) were designed. These four oligonucleotides encode the E. coli DsbA signal sequence. The E. coli DsbA protein can be found in the Swiss-Prot database (accession number P24991). Its signal sequence is MKKIWLALAG LVLAF-SASA (SEQ ID NO:1). The oligonucleotides oDST4, oDST5, oDST6, and oDST8 were annealed and amplified with oligonucleotides oDST6 and oDST8 by PCR. The resulting DNA fragment encodes the DsbA signal sequence and is flanked by the restriction endonuclease sites XbaI and BamHI. This DNA fragment was digested with XbaI and BamHI and ligated into the similarly treated and dephosphorylated pAK100 derivative. The resulting phagemid pDST23 (FIG. 3) was isolated and the correct sequence was verified by DNA sequencing.

To allow direct experimental comparison to phagemids encoding the signal sequence of PhoA (SEQ ID NO:9), a second phagemid called pDST22 was generated. Again, four oligonucleotides—called oDST4p (SEQ ID NO:10), oDST5p (SEQ ID NO:11), oDST6 (SEQ ID NO:7), and oDST8p (SEQ ID NO:12)—were annealed and amplified with oDST6 and oDST8p by PCR. The resulting DNA fragment encodes the PhoA signal sequence and is flanked by the restriction endonuclease sites XbaI and BamHI. This DNA fragment was digested with XbaI and BamHI and ligated into the similarly treated and dephosphorylated pDST23. The resulting phagemid pDST22 was isolated and the correct sequence was verified by DNA sequencing.

The other phagemids used in this study are listed in Table 1 and were obtained as follows: The coding sequences of the proteins of interest were PCR amplified using appropriate designed PCR primers and template DNA, such as prepared cDNA or public available plasmid DNA. Thereby, either a BamHI or a BglII restriction sites was introduced 5-prime to each of the coding sequences and two restriction sites (EcoRI and PstI) were introduced 3-prime to each of the coding sequences. These PCR fragments were digested either with BamHI or BglII and either EcoRI or PstI, and then ligated into the similarly treated and dephosphorylated phagemids pDST23 or pDST22. The open reading frame of the expression cassette for the fusion polypeptide comprising the cloned PCR product was maintained for all constructs, especially the correct reading frame for the C-terminal fusion to the C-terminal domain of phage protein III (CTp3) was maintained. The first and the last amino acids of the cloned proteins of interest are given in Table 1 as well as the reference or accession number for either the GenBank orthe Swiss-Prot databases. The correct sequence of all phagemids was verified by DNA sequencing.

For the designed ankyrin proteins (DARPins) 3a and 2_3, phagemids encoding the PelBss (pDST80 and pDST81, respectively), SfmCss (pDST86 and pDST87, respectively), TolBss (pDST84 and pDST85, respectively) and TorTss (pDST88 and pDST89, respectively) were generated, using the same cloning strategy as described above for DsbAss and PhoAss.

Phage Production and Purification 5 ml 2xYT medium containing 1% glucose, 34 µg/ml chloramphenicol (cam) and 15 µg/ml tetracycline (tet) were inoculated with a single colony of E. coli XL-1 Blue harboring the phagemid of interest and the cells were grown overnight at 30° C. with shaking. Fresh 5 ml 2xYT medium containing 1% glucose, 34 µg/ml cam and 15 µg/ml tet were inoculated with the overnight cultures at a ratio of 1:100 ($OD_{600}$=0.04) and grown at 37° C. to an $OD_{600}$ of 0.5 with shaking. The cultures were infected with VCS M13 helper phage at $4 \times 10^{10}$ pfu (plaque forming units) per ml (multiplicity of infection ~20) and the cells were incubated for 30 min at 37° C. without agitation and then for 30 min at 37° C. with shaking. The medium was changed by harvesting the cells by centrifugation (3500 g, 24° C., 10 min) and resuspending the pellet in 50 ml of 2xYT medium containing 34 µg/ml cam, 50 µg/ml kanamycin (kan) and 0.1 mM isopropyl-β-D-thiogalactoside (IPTG). After growth for 14 to 16 h at 30° C. with shaking, the cells were removed by centrifugation (5600 g, 4° C., 10 min). The culture supernatant was incubated on ice for 1 h with one-fourth volume of ice-cold PEG/NaCl solution (20% polyethyleneglycol (PEG) 6000, 2.5 M NaCl). The precipitated phage particles were then collected by centrifugation at (5600 g, 4° C., 15 min) and redissolved in 1 ml of $TBS_{150}$ (25 mM Tris/HCl, 150 mM NaCl, pH 7.5). Further purification of the phage particles was done by CsCl gradient centrifugation as follows. After addition of 1.6 g of CsCl, the volume was adjusted to 4 ml with $TBS_{150}$. The CsCl solution was transferred into a ½×1½ inch polyallomer tube (Beckmann, USA, No 358980) and centrifuged at 100000 r.p.m. for 4 h in a TLN-100 rotor (Beckman Instruments) at 4° C. After centrifugation the phage band was recovered. The phages were transferred to ½×2 inch polycarbonate tubes (Beckmann, USA, No 349622), which were filled with $TBS_{150}$ to 3 ml. After centrifugation at 50000 r.p.m. for 1 h in a TLA-100.3 rotor at 4° C., the pelleted phages were redissolved in 3 ml TBS. After an additional centrifugation at 50,000 r.p.m. for 1 h in a TLA-100.3 rotor at 4° C., the phages were dissolved in 1 ml TBS. The total concentration of phage particles was quantified spectrophotometrically. The infective titer of the phage samples was determined by titration on E. coli XL-1 Blue cells using 2xYT agar plates containing 1% glucose and 34 µg/ml cam. The colonies were counted after overnight incubation at 37° C.

Phage Blots $5 \times 10^{11}$ phage particles, purified by CsCl gradient, were applied to 15% sodium dodecyl sulfate polyacrylamide gel electrophoresis (SDS-PAGE) under reducing conditions and transferred to a polyvinylidene fluoride (PVDF) Immobilon-P Transfer Membrane (Millipore, USA) by electroblotting. The membrane was blocked with $MTTBS_{150}$ ($TBS_{150}$, 0.1% Tween 20, 5% skimmed milk) for 1 h at room temperature (RT) and incubated with a murine anti-pIII antibody (MoBiTec, Germany, No. PSKAN3) (1:1000 in $MTTBS_{150}$, 20 min at RT) as primary antibody, which recognizes the C-terminal domain of pIII. A F(ab')$_2$ fragment goat anti-mouse IgG horseradish peroxidase conjugate (Pierce, USA, No. 31438) (1:10000 in $MTTBS_{150}$, 1 h at RD was used as secondary antibody. The proteins were detected with Chemi-Glow West substrate (Alpha Innotech, USA).

In a second experiment, the blocked membrane was incubated with murine anti-FLAG M1 antibody (Sigma, USA, No. F3040) (1:5000 in $MTTBS_{150}$, 1 h at RD as primary antibody. A goat anti-mouse IgG alkaline phosphatase conjugate (Sigma, USA, No. A3562) (1:10000 in $MTTBS_{150}$, 1 h at RT) was used as secondary antibody. The proteins were detected with the substrates 5-bromo-4-chloro-3-indolyl phosphate (BCIP) and nitro blue tetrazolium (NBT) (Fluka, Switzerland).

Phage ELISA

Phage ELISAs were carried out to assay the amount of functionally displayed DARPins on M13 phage particles. Biotinylated APH and JNK2 proteins (Binz et al., loc. cit.) were immobilized as follows: Neutravidin (66 nM, 100 µl/well; Socochim, Switzerland) in $TBS_{150}$ was immobilized on MaxiSorp plates (Nunc, Denmark, No. 442404) by overnight incubation at 4° C. The wells were blocked with 300 µl $BTTBS_{150}$ ($TBS_{150}$, 0.1% Tween 20, 1% BSA) for 1 h at room temperature. Binding of the biotinylated APH and JNK2 proteins (100 µl, 1 µM) in $BTTBS_{150}$ was done for 1 h at 4° C.

Dilution series of phage particles in $BTTBS_{150}$ were added to the wells and incubated at RT for 2 h. After washing the wells five times with 300 µl $TTBS_{150}$ ($TBS_{150}$, 0.1% Tween 20) for 5 min, bound phage particles were detected with anti-M13 horseradish peroxidase conjugate (Amersham Pharmacia Biotech, UK, No. 27-9421-01) and soluble BM Blue POD substrate (Roche Diagnostics, Germany, No. 1484281).

Phage Panning

E3_5, E3_19, 3a and 2_3 displaying phage particles were produced from either phagemids encoding the PhoA signal sequence (pDST30, pDST65, pDST22, pDST34) or from phagemids encoding the DsbA signal sequence (pDST32, pDST66, pDST23, pDST37), respectively. These phage particles were used to prepare mixtures of phage particles produced from phagemids encoding either PhoAss or DsbAss. To a 1:1 mixture of phage particles displaying the non-binding DARPins E3_5 and E3_19, phage particles displaying the target-specific DARPins 3a or 2_3 were added in a $1:10^7$ dilution. Biotinylated APH and JNK2 proteins were coated as described for the phage ELISA. To each well 0.1 ml of phage particle mixtures ($10^{13}$ cfu/ml) were added to 0.1 ml $BTTBS_{150}$ and incubated for 2 h. After washing (3 times for the first selection cycle, 4 times for the second cycle and 5 times for additional cycles) with $TTBS_{150}$ and (3 times for the first selection cycle, 4 times for the second cycle and 5 times for additional cycles) with $TBS_{150}$, the phage particles were eluted by incubating for 15 min with 0.2 ml elution buffer (0.2 M glycine/HCl, pH 2.2) at about 22° C. followed by an elution for 30 min with 0.2 ml trypsin (10 mg/ml in $TBS_{150}$) at 37° C. The combined eluates (neutralized with 10 µl of 2 M Tris-base) were used for the infection of 4 ml of exponentially growing E. coli XL1-Blue. After 30 min at 37° C. without agitation and 30 min at 37° C. with shaking, the cells were spread on 2xYT agar plates containing 1% glucose and 34 µg/ml cam and 15 µg/ml tet and grown overnight at 37° C. The cells were washed from the plates with 2xYT containing 1% glucose, 15% glycerol, 34 µg/ml cam and 15 µg/ml tet and used for the phage production for the next cycle of panning. After each panning cycle, the identity of 9 to 16 eluted phage particles was determined. This was done by infection of E. coli with these phage particles and screening of the colonies by PCR with clone-specific primers.

The invention claimed is:

1. A filamentous phage library display method for polypeptides of interest comprising the steps of
   (a) constructing a filamentous phage or phagemid vector containing an expression cassette for a fusion polypeptide comprising a polypeptide of interest and an N-terminal signal sequence promoting cotranslational translocation of the fusion polypeptide across a cytoplasmic membrane of a Gram-negative bacteria,
   wherein the signal sequence promoting cotranslational translocation is based on the signal recognition particle pathway is selected from the group consisting of signal sequences of TorT, SfmC, FocC, CcmH, Yral, TolB, NikA, FlgI, and DsbA;
   (b) constructing a combinatorial library of phage or phagemid vectors by cloning of a DNA library encoding polypeptides of interest into the expression cassette of a plurality of vectors of step (a), wherein said DNA library is a cDNA library or a combinatorial DNA library that encodes a library based on alternative scaffolds;
   (c) transforming suitable Gram-negative bacteria with the library of vectors of step (b)
   wherein the polypeptides of interest encoded by the DNA library are cotranslationally translocated across the cytoplasmic membrane of Gram-negative bacteria, and wherein the polypeptides of interest are displayed on phage particles; and
   (d) performing phage display selection cycles to separate the phage particles based on properties of the displayed polypeptides of interest.

2. The method of claim 1 wherein the signal sequence is selected from the group consisting of signal sequences of TorT, SfmC, TolB and DsbA.

* * * * *